US005104394A

United States Patent [19]

Knoepfler

[11] Patent Number: 5,104,394

[45] Date of Patent: Apr. 14, 1992

[54] AUTOMATIC STAPLER FOR LAPAROSCOPIC PROCEDURE WITH SELECTIVE CUTTER AND SUCTION IRRIGATOR

[76] Inventor: Dennis J. Knoepfler, 1383 Whitaker La., Amelia, Ohio 45102

[21] Appl. No.: 609,363

[22] Filed: Nov. 5, 1990

[51] Int. Cl.[5] .......... A61B 17/00

[52] U.S. Cl. .......... 606/143; 606/167; 227/180

[58] Field of Search .......... 606/142, 139, 143; 227/19, 175-180

[56] References Cited

U.S. PATENT DOCUMENTS

| | | | |
|---|---|---|---|
| 3,775,825 | 12/1973 | Wood et al. | 606/142 |
| 3,777,538 | 12/1973 | Weatherly et al. | 606/142 |
| 3,882,854 | 5/1975 | Hulka et al. | 128/6 |
| 3,889,683 | 6/1975 | Kapitanov et al. | |
| 4,111,206 | 9/1978 | Vishnevsky et al. | 227/19 |
| 4,244,372 | 1/1991 | Kapitanov et al. | 227/19 |
| 4,246,903 | 1/1981 | Larkin | 606/142 |
| 4,429,695 | 2/1984 | Green | 227/19 |
| 4,556,058 | 12/1985 | Green | 227/19 |
| 4,608,981 | 9/1986 | Rothfuss et al. | 227/19 |
| 4,633,874 | 1/1987 | Chow et al. | 227/19 |
| 4,644,951 | 2/1987 | Bays | 604/22 |
| 4,990,153 | 2/1991 | Richards | 606/148 |

OTHER PUBLICATIONS

Ethicon Ad: "Now, Ethicon Titanium Staples Complete the Picture".

Ethicon Ad: "A New Sense of Security in Endoscopic Litigation".

*Primary Examiner*—Stephen C. Pellegrino
*Assistant Examiner*—Gary Jackson
*Attorney, Agent, or Firm*—Wood, Herron & Evans

[57] ABSTRACT

An improved surgical stapler is disclosed which is particularly suitable for use in laparoscopic procedures. The stapler includes a handle and an elongated shaft and jaws at its distal end which are adapted to close staples. This improved stapler further includes a cutter which is adapted to cut items grasped by the jaws. The jaws are actuated independently of the stapling mechanism. This substantially improves the versatility of this device. A suctioning tube is also provided at the tip of the apparatus. This device permits surgeons to staple and subsequently selectively cut without removing the instrument.

5 Claims, 3 Drawing Sheets

58 16 56 45 43 15 41 42 44 57 116 117 14 20 13 19

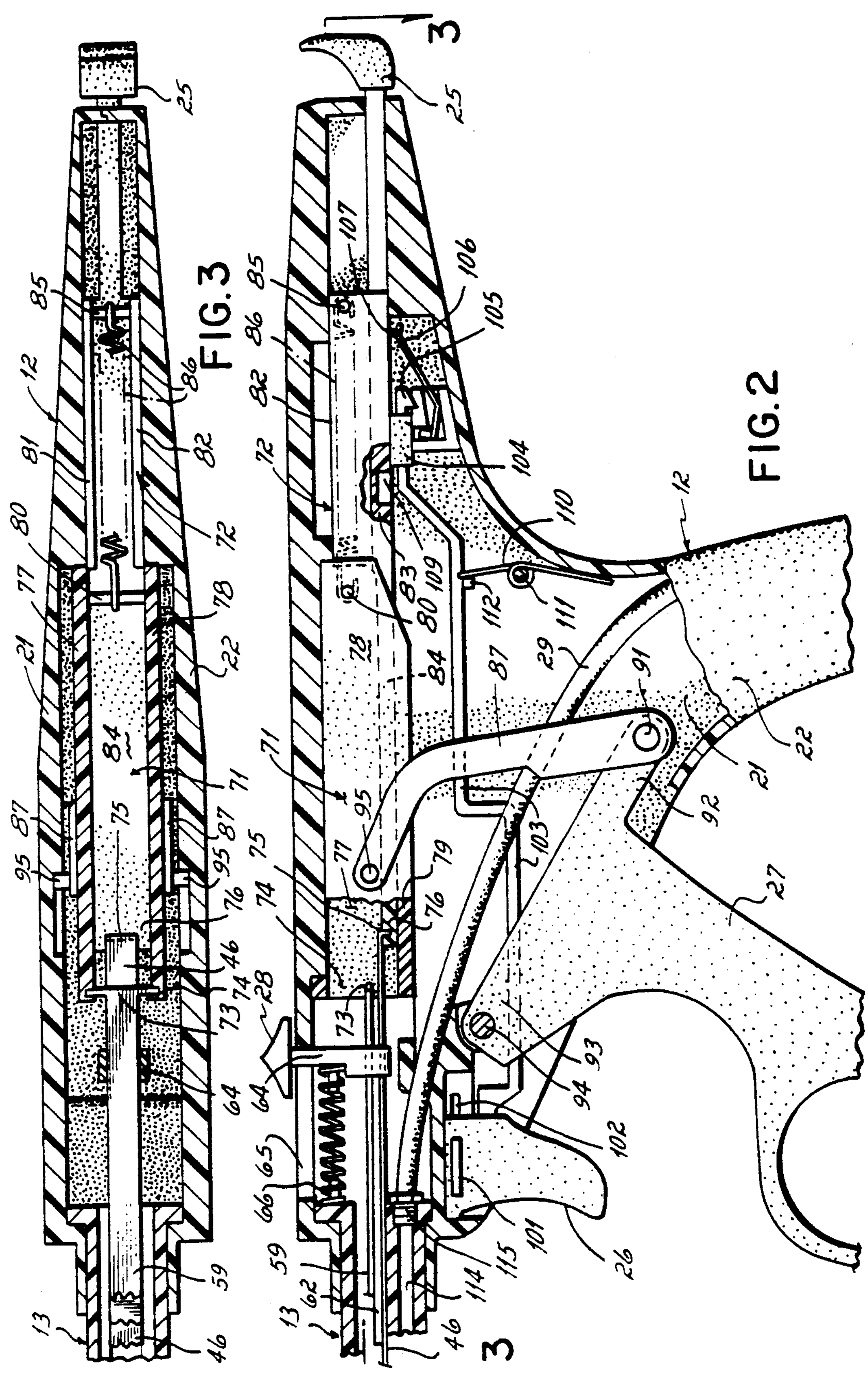

62
59
46
38
32
13
19
20
62
5
35
48
52
46
59
47
33
6
31
6
30a, 30b
58
50
14
61
16
45
57
44
15
5

59
60
63
62
53
48
13
52
47
55
54
58
57
56
14
44
45
43
15

13
62
45
114
52
59
30a
19
49
46
31
20
33
30b 33
31
36
37
39
34
37
40

AUTOMATIC STAPLER FOR LAPAROSCOPIC PROCEDURE WITH SELECTIVE CUTTER AND SUCTION IRRIGATOR

BACKGROUND

The use of surgical staplers in place of sutures is now commonplace. There are a variety of different types of staplers which are employed for various types of operations. For laparoscopic procedures, uniquely designed apparatus are required.

In a laparoscopic procedure, the instruments must fit through a cylindrical cannula into the body cavity. They must be elongated and generally conform to the shape of the cannula and therefore must be generally cylindrical. Such surgical staplers exist.

Due to the nature of laparoscopic procedures, it is undesirable to repeatedly insert and remove instruments from the cannula. The surgeon cannot directly view the organ or area of operation. Therefore, the surgeon must locate and relocate vessels and other body parts which are the subject of operative procedures. When a cystic duct, for example, is sutured and cut, the cystic dust must be sutured or stapled at two locations; then the stapler must be removed and a cutting device inserted to cut between the two staples. This is particularly time consuming, requiring that the stapler be removed and the cutter be inserted and each time the bile duct be relocated.

Accordingly, it is an object of the present invention to provide a laparoscopic device which will both staple and cut.

It is further an object of the present invention to provide a laparoscopic stapler which will permit the stapler to independently grasp body parts irrespective of the stapling operation.

Further, it is an object of the present invention to provide for a surgical stapler which will grasp a body part and permit the cutter to be selectively operated to cut the body part when grasped by the stapler. This provides an apparatus which can grasp a body part, staple it, and hold it while it is being cut. Further, the present invention permits this to occur in any sequence.

It is also the object of this invention to enable suctioning and irrigating through a separate channel.

The objects and advantages of the present invention will be further appreciated in light of the following detailed description and drawings in which:

DETAILED DESCRIPTION OF THE DRAWINGS

FIG. 1 is a side plan view of the present invention;

FIG. 1*a* is an enlarged perspective view of the tip end portion of FIG. 1;

FIG. 2. is an enlarged longitudinal cross sectional view of the grip portion of FIG. 1;

FIG. 3 is an overhead cross sectional view taken at lines 3—3 of FIG. 2;

DETAILED DESCRIPTION

Figure 1:
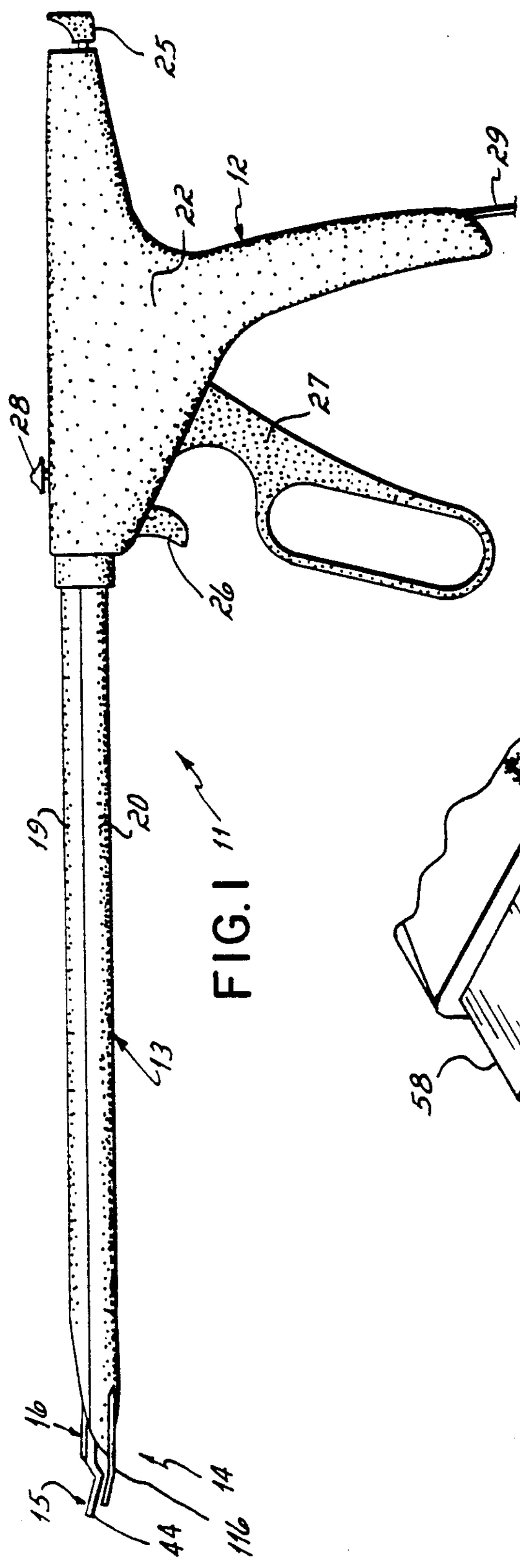

As shown in FIG. 1, the present invention is a laparoscopic stapler 11 which includes a grip portion 12, cylindrical shaft 13 and a tip portion 14. The tip portion includes jaws 15 and a cutting blade 16.

The shaft 13 which runs between the tip 14 and the grip portion 12, includes a top semi-annular portion 19 and a bottom semi-annular portion 20. The handle 12 is a two-piece plastic handle. It includes a first handle housing 21 and a mirror image handle housing 22 which are fixed together. The grip portion 12 includes a staple feed latch activator 25, a trigger 26 which acts to advance staples and scissors grip 27 which acts to close the jaw 15 which will both act as a clamp and act as a staple closer. Grip portion 12 also includes a thumb slide 28 which advances the cutter 16. Also extending into the grip portion is a vacuum tube 29. Of course this tube will need a lever locke cap to prevent evacuation of the pneumo-peritoneum.

The trigger 26, scissors grip 27 and thumb slide 28 act to operate elements within shaft 13 to in turn operate elements in the tip 14.

Figure 4:
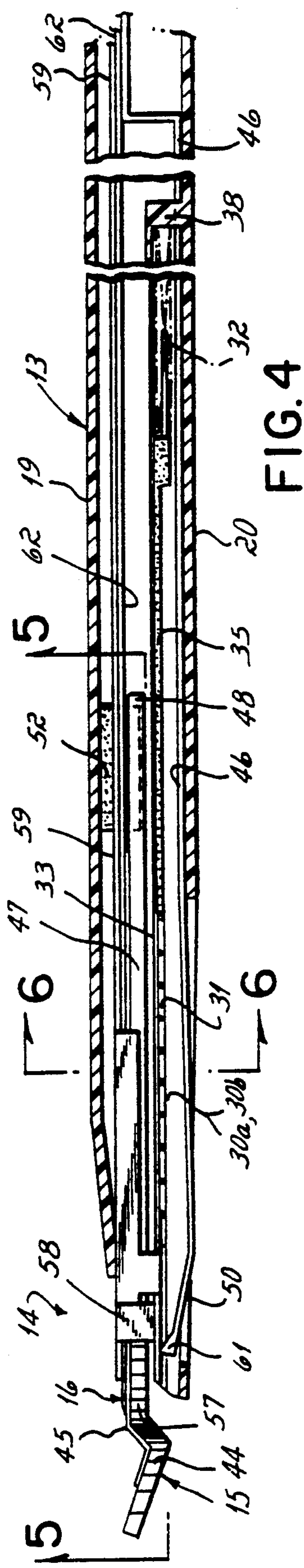
FIG. 4 is an enlarged longitudinal cross sectional view (partially broken away) of the shaft end of FIG. 1.
Figure 5:
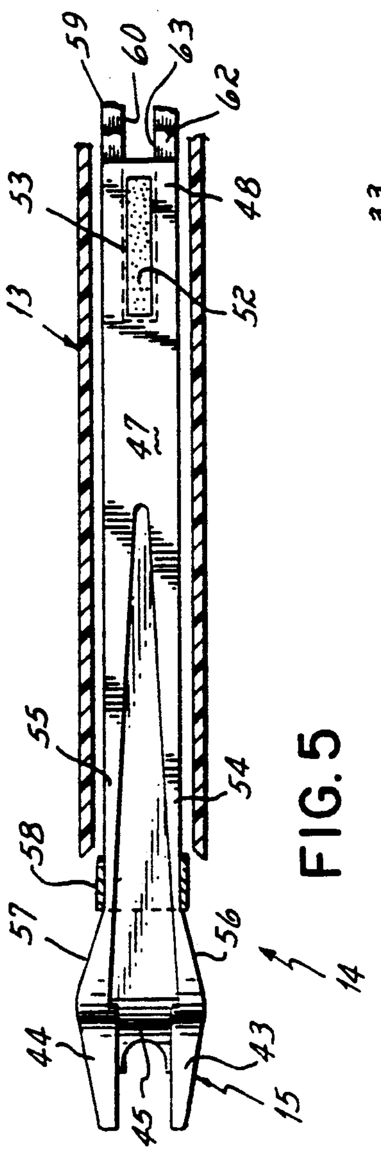
FIG. 5 is a bottom cross sectional view taken at lines 5—5 of FIG. 4.
Figure 6:
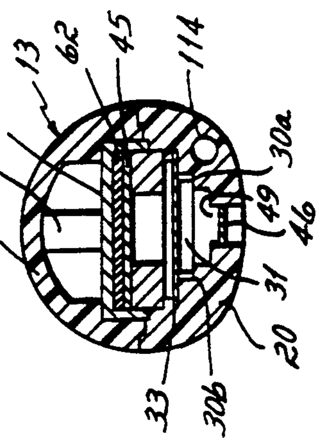
FIG. 6 is a cross sectional view taken at lines 6—6 of FIG. 4.
Figure 7:
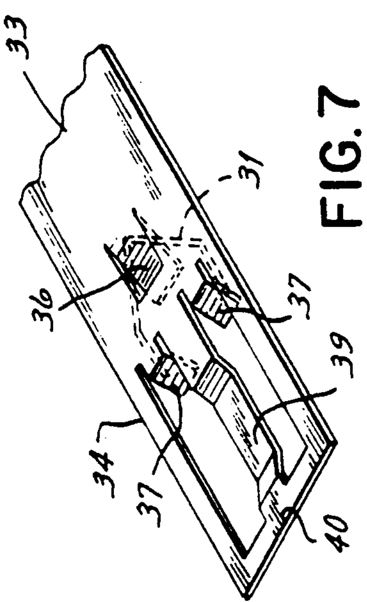
FIG. 7 is a fragmentary perspective view of the forwardmost end of the staple retaining member of the feed mechanism.

As shown more particularly in FIGS. 4, 5, and 6, the lower or bottom half 22 of shaft 13 holds a plurality of four-sided v-shaped staples 31 which are aligned one behind another in a planar position in bottom half 22. In order to provide this magazine of staples 31, the bottom half 22 is covered with a metal strip 33. Strip 33 is compression fitted to shaft portion 22 separating it from the upper shaft portion 21. Shaft portion 22 includes molded ledge portions 30*a*, 30*b*, shown in FIG. 6 below strip 33. The staples ride on the ledge portions 30*a* and 30*b*.

A compressed spring 32 runs between a staple feed finger 35 at the rear of the staples 31 and an internal abuttment 38 of shaft portion 22 urging the feed finger and staples towards the tip 14.

The forward portion 34 of metal strip 33 includes a first rearward tab 36 and two forward tabs 37. Between the two forward tabs 37 is a central member 39 which is bent downwardly into the lower shaft portion 22 and extends to the forward most edge 40 of strip 33. Edge 40 lies adjacent to first and second staple channels 41 and 42 which run along jaw members 43 and 44 of jaw 15.

As best seen in FIG. 4, the jaw 15 is formed from a metal strip 47 (preferably formed from spring steel), which has a rear portion 48, and two forward prongs 54 and 55. The forward prong 54 and 55 terminate at their end tips to form the jaw portions 43 and 44. The rear portion 48 of metal strip 47 includes a hole 53 which snaps onto a boss 52 extending from the top 21 of shaft 13. Welded to the metal strip 47, forward of the hole 53, is a guide strip 45 which extends forward to the jaw 15. This strip acts to assist staples to remain in the staple channels 41 and 42.

A cutting strip 62, having at its outer or forward end the cutting edge 16, lies above the guide strip 45 and extends to the tip 14. A slot 63 in cutting strip 62 allows it to slide forwardly and reawardly without contacting the boss 52. A collar 58 wraps around the cutting strip 62, metal strip 45 and first and second prongs 54 and 55. The rear portion of this collar is a metal strip 59, also having a slot 60 to surround boss 52, which extends into the handle portion 12.

The prongs 54 and 55 forward of collar 58 include laterally flared portions 56 and 57 which are wider than the width of collar 58. Thus, since the metal strip 47 is fixed through boss 52 relative to shaft 13 and collar 58 can slide relative to shaft 13 and metal strip 47, the jaws close together when collar 58 is forced forwardly by strip 59. The operation of this apparatus will be described in more detail below.

Also in the lower portion 22 of shaft 13 is a staple advancing strip 46. Staple advancing strip 46 runs in a channel 49 immediately beneath spring 32. The forward most portion 50 of staple advancing strip 46 is bent downwardly through a channel in lower portion 22 and then upperwardly. The extreme forward tip of strip 46 has a head portion 61 which is adapted to engage and push a staple along the ledge portions 30*a* and 30*b* up into the staple engaging channels 41 and 42 of jaw members 43 and 44.

The grip portion 12 includes all the mechanism adapted to operate the various elements running through the shaft 13 to the tip 14.

The cutter 16 is advanced independently of all other operations. Thumb slide 28 includes a leg portion 64 which extends downwardly through slot 65 into the grip portion 12 and engages cutting strip 62. As shown, slide 28 includes upper and lower rectangular passages which permit the metal strips 46 and 59 to move freely relative to thumb slide 28.

Thumb slide 28 is urged by spring 66 in a rearward position which maintains the cutting edge 16 in a nonengaged position.

The metal strips 46 and 59 are connected to interacting plastic outer and inner carriages 71 and 72, respectively. Strip 59 includes a rear tip portion 73 which is snapped fit onto the forward portion 74 of outer carriage 71. The rear tip 75 of strip 46 extends through portion 74 of outer carriage 71 and snap fits into the forward end 76 of the second or inner carriage 72.

The outer carriage 72 includes two side walls 77 and 78 and a bottom wall 79. Between side walls 77 and 78 extends a pin 80.

The inner carriage 72 also includes two side walls 81 and 82, a bottom wall 83 and a forward portion 84. Between side walls 81 and 82 is a pin 85. Connecting pin 85 of carriage 72 with pin 80 of carriage 71 is a spring 86 which urges the two carriages together (the position shows in the Figs.).

The forward portion 84 of the inner carriage is low enough to slide under pin 80 and extend almost up to the forward most portion 74 of carriage 71.

The carriages are independently moved relative to grip portion 12 by a pair of linkages 87 and actuator 25. The outer carriage 71 can be urged forwardly by left and right carriage linkages 87. The inner carriage 72 is urged rearwardly by pulling the actuator 25. Left and right carriage linkages 87 are mirror images which are fixed to the left and right side of scissors grip 27. Therefore only the left carriage linkage is shown and described.

More particularly, a first end of the linkage 87 is pivotably connected by a pin 91 to an arm 92 of scissors grip 27. A second arm 93 of grip 27 is pivotably attached to the housing 12 by a pin 94. The scissors grip 27 can rotate relative to this pin 94. Thus, as it rotates relative to pin 94, arm 92 moves upperwardly urging links 87 upperwardly.

The second end of linkage 87 is rotatably connected by pin 95 to side wall 78 of carriage 71. The mirror image linkage 87 is attached to the opposite side walls 77, 78 of the carriage.

The housing also includes trigger 26. Trigger 26 includes a planar extension 101 on either side that slides in channels 102 in the housing 12. This trigger pushes a pusher bar 103 rearwardly. The rearward most portion of the pusher bar includes a slide bushing 104 and a tip portion 105. Tip portion 105 is adapted to engage a spring clip 106 pushing its tip 107 downwardly. The spring clip 106 is held in a clip bracket formed in the housing 12 which presses the tip 107 upwardly.

When the carriage 72 is pulled back by the actuator 25, the spring clip 106 being urged upperwardly engages a slot 109 in the bottom of carriage 72 holding it in a rearward position. When trigger 26 is pushed back, its tip 105 engages the spring clip 106 pushing it down allowing the carriage 72 to move forwardly. A spring 110 held by pin 111 engages a lateral protrusion 112 of pusher rod 103 keeping the trigger urged in a forward position.

Figure 1A:
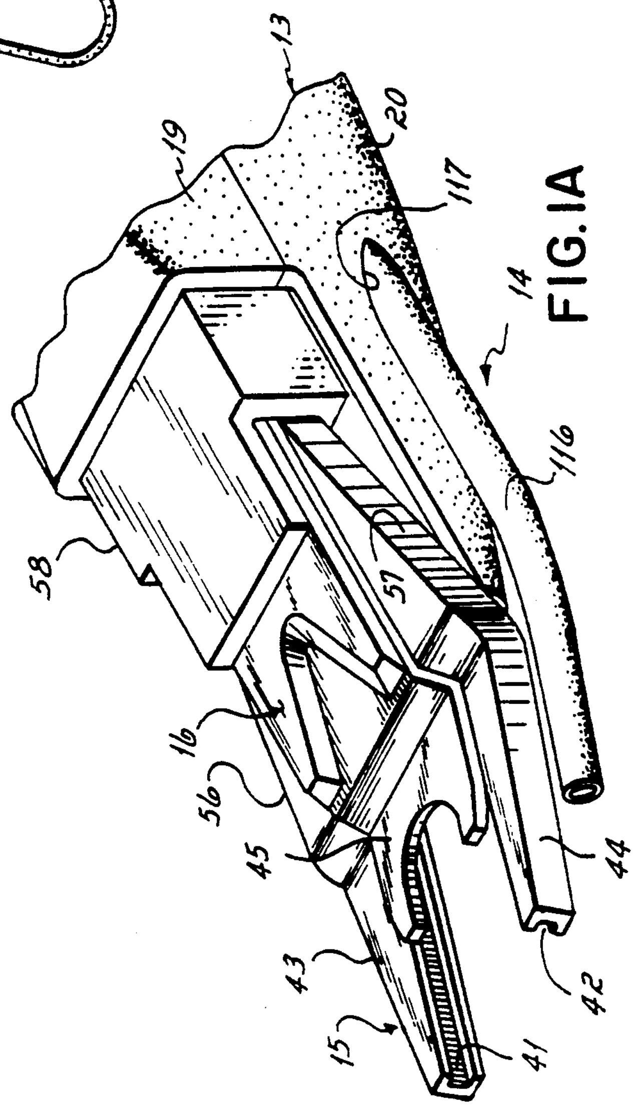

Extending through the housing is the flexible irrigation/vacuum tube 29 which extends to the shaft 13. The shaft 13 includes a molded passageway 114 into which the tube 29 is fixed by a fitting 115. The passageway extends the length of the shaft 13. As shown in FIG. 1*a*, a rigid tube 116 is fixed by adhesive or some welding to the distal end 117 of passageway 114. Thus, the tip portion 14 is connected to a suction irrigating system (not shown) to permit irrigation and suction of material from the area being worked on.

In operation, the scissors grip 27 is pulled rearwardly. This pushes the arm 92 upperwardly and forcing linkages 87 upperwardly. Linkage 87 acts to force carrier 71 forwardly. When the carriage 71 is urged forward, it will push the metal strip 59 forwardly. This in turn will cause the collar 58 to move forwardly and engage the flared portion 56 and 57 of jaw 15. This will force the prongs 54 and 55 together.

Release of the grip 27 permits the spring 86 to pull the carriage 71 towards carriage 72 pulling with it the strip 59 and collar 58. Since the prongs 54 and 55 are formed from spring metal, they will open back up. If when the jaws are closed it is desired to cut something, the thumb slide 28 is pushed forwardly causing blade 16 to advance and contact whatever is being grasped by the jaws 54 and 55.

To advance a staple 31, the actuator 25 is grasped and pulled rearwardly, pulling with it the inner carriage 72 and extending the spring 86. This rearward movement of carriage 72 will engage the spring 106 into slot 109 to hold the carriage in its latched rearward position. The side walls of carriage 71 engage an extension 115 in the housing 12 which prevents the carriage 71 from being pulled rearwardly towards carriage 72. The trigger 26 is pulled backwardly which will push the pusher arm 103 rearwardly causing its rear tip 105 to engage the spring clip 106 forcing it down out of slot 109. Thus, carriage 72 will be pulled by spring 86 forwardly and in turn push strip 46 forwardly. The tip 61, when in a rearward position, would engage the rear of the staple 31 and push it along ledges 30*a* and 30*b* into staple channels 41 and 42. The guide strip 33 would help maintain these in position.

Thus at this point, the staple would be lodged in channels 41 and 42. If the grip 27 is pressed, the linkages 87 would force the the carriage 72 to close on the flared portions 56 and 57 causing prongs 54 and 55 to close forcing the staple together.

In an operative procedure, this provides many unique advantages. A vessel can be first stapled with a first staple, stapled with a second staple and while still being grasped can be cut with cutter 16. Futher, if one wants to cut something without stapling, the item can be grasped and cut without any staple being put into position. This eliminates the need of inserting the stapler, positioning a second staple, removing the stapler, locating the stapled areas, grasping this and cutting it. This substantially reduces the time required to proceed with the operative procedure. Further, the irrigation/vacuum tube permits the area to be evacuated and irrigated as needed. This is particularly significant since the area which would require evacuation would be the area the stapler and cuter were contacting. Particularly if there was a blood vessel nicked during the procedure, this would permit the blood to be quickly removed without removing the stapler.

Further, the combination of independently acting jaws to hold a vessel and a single blade to cut the vessel is particularly suited for laparoscopic procedures. This means of cutting is significantly better than a scissors type of cutting since only one blade moves in a forward direction as opposed to two blades moving laterally toward each other.

This instrument is particularly useful in lysing adhesions, incising peritoneal linings of gallbaldders or of small bowel mesentery. It is also useful for dissecting, stapling and dividing bowel mesentery for future bowel resection.

The preceeding has been a description of the present invention along with a preferred method of practicing the invention, however, it should be defined only by the appended claims wherein we claim:

1. A surgical stapler for use in laparoscopic surgery comprising a grip portion, a tip portion and a shaft portion extending between the grip portion and the tip portion said tip portion including a staple advancing means and a pair of jaws adapted to close and bend staples and to act as a clamp; a cutter adapted to move forwardly along said jaws to cut tissue held by said jaws;

said grip portion comprising means to advance said cutter; means to activate said staple advancing means and means to independently close said jaws both when a staple is in place and when no staple is in place.

2. The stapler claimed in claim 1 further comprising a vacuum tube extending through said shaft to said tip portion.

3. The stapler claimed in claim 1 wherein said cutter advancing means is spring biased in a retracted position.

4. A laparoscopic cutting instrument comprising a grip portion, a tip portion and a shaft portion;

said tip portion including a spring biased pair of jaws operable by means of a collar slidably engaging said jaws;

a cutter comprising an elongated pusher extending the length of said shaft portion and have a forward most cutting tip adapted to slide along said jaws;

wherein said grip portion includes means to slide said collar forwardly to close said jaws and means to move said pusher forwardly and rearwardly.

5. The cutting instrument claimed in claim 4 further comprising means to advance staples between said jaws.

* * * * *